US00PP31756P2

(12) United States Plant Patent
Hansen

(10) Patent No.: US PP31,756 P2
(45) Date of Patent: May 12, 2020

(54) ***ACHILLEA* PLANT NAMED 'PETER COTTONTAIL'**

(50) Latin Name: *Achillea ptarmica*
Varietal Denomination: Peter Cottontail

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,801

(22) Filed: Jan. 14, 2019

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14
See application file for complete search history.

*Primary Examiner* — Anne Marie Grunberg

(57) ABSTRACT

The new and distinct Yarrow plant named *Achillea* 'Peter Cottontail', dense mounded habit, of upright heavily branched stems of medium height; linear, serrate, slightly-glossy, deep-green leaves; heavy flowering of white, predominately sterile flowers in large heads averaging over 100 florets per head beginning in mid-June and continuing for nearly seven weeks. The new plant is useful as a specimen landscape plant, mass planting or cut flower in arrangements.

1 Drawing Sheet

Botanical designation: *Achillea ptarmica.*
Cultivar denomination: 'Peter Cottontail'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Feb. 1, 2018 the claimed plant was displayed as a photograph and brief non-enabling description on a website maintained by Walters Gardens, Inc., who obtained the plant and all information relating thereto, from the inventor. No plants of *Achillea* 'Peter Cottontail' have been sold, in this country or anywhere in the world, nor has any disclosure of the new plant been made, more than one year prior the filing date of this application, and such sale or disclosure within one year. was either derived directly or indirectly from the inventor.

BACKGROUND OF THE PLANT

The present invention relates to the new and distinct yarrow herein also referred to as *Achillea* 'Peter Cottontail', by the cultivar name, 'Peter Cottontail', or as the new plant. The new plant was the result of a cross by the inventor between H10-01 (not patented) and H10-02 (not patented) on Jun. 23, 2014 and harvested in September of 2014. The new plant is a single seedling selection among several in that cross identified by the breeder code 14-73-2 through the trial process.

Asexual propagation at the same nursery in Zeeland, Mich., USA by cuttings has shown 'Peter Cottontail' to be stable and reproduce true to type in successive generations.

SUMMARY OF THE PLANT

*Achillea* 'Peter Cottontail' has not been observed in all possible environmental conditions. The phenotype may vary slightly with changes in environments such as light intensity, fertility, water availability, etc. without, however any variation in genotype.

*Achillea* 'Peter Cottontail' is distinct from all cultivars known to the inventor in the following combined traits:

1. Dense mounded habit of upright stems with medium height.
2. Linear, serrate, slightly glossy leaves of deep green.
3. Heavily-branched flower stems cover plant in white, predominately sterile, large flower heads during peak flowering.
4. Heavy flowering of white, predominantly sterile flowers in large heads.
5. Long flowering period beginning in mid-June and continuing for nearly seven weeks.

Plants of *Achillea* 'Peter Cottontail' are most similar to 'Gipi Whit' U.S. Plant Pat. No. 18,120, 'The Pearl' (not patented) and 'Noblessa' (not patented). 'Gipi Whit' U.S. Plant Pat. No. 18,120 has a smaller habit of less than half of that of the new plant and fewer inflorescences per stem and per plant. 'The Pearl' has less doubling of the flower, fewer florets per capitulum, and is less compact than the new plant. 'Noblessa' is shorter and narrower in habit and tends to be less double in flower. 'Ballerina' (not patented) is a seed group that tends to produce more fertile flowers with smaller flower heads, fewer florets per capitulum, and slightly shorter habit. 'Double Diamond' (not patented) is a seed group that tends to be taller in habit and produce more fertile flowers. 'Peter Cottontail' has broader flower petals than all of the above comparison varieties known to the inventor.

BRIEF DESCRIPTION OF THE DRAWINGS

The color drawings illustrate the overall characteristics of *Achillea* 'Peter Cottontail' as a three-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
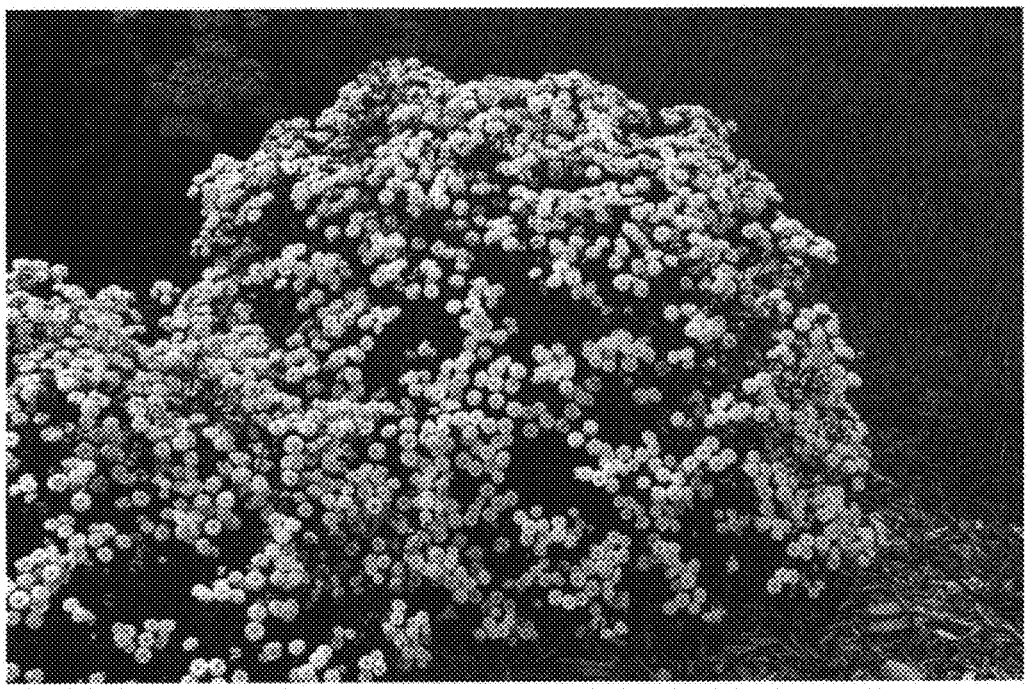
FIG. 1 shows the new plant in a landscape environment.
Figure 2:
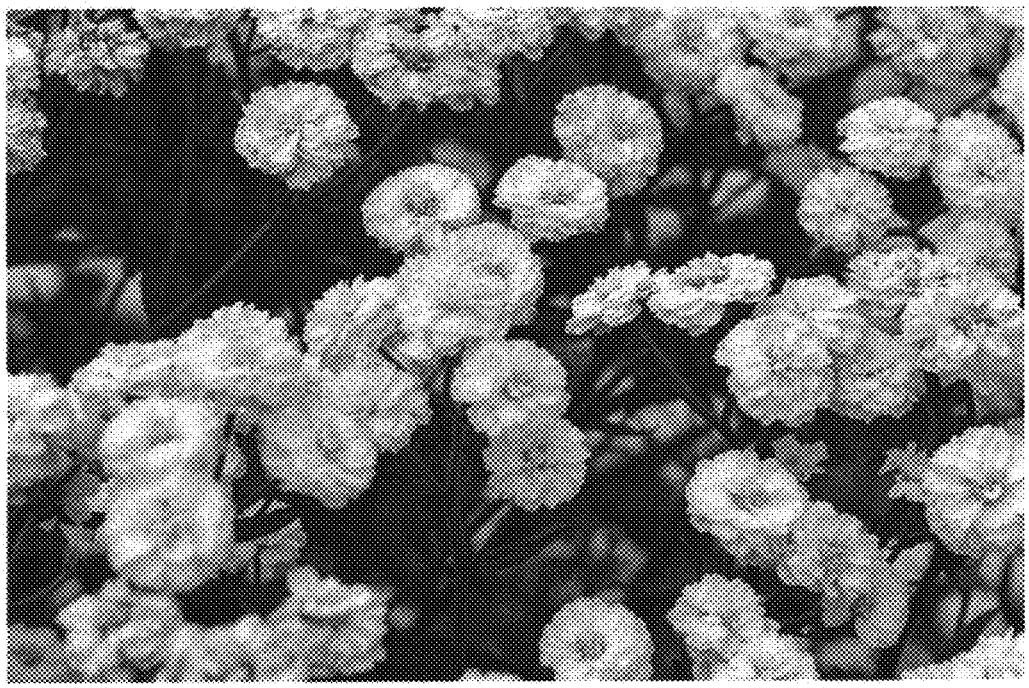
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent is H10-01; male or pollen parent is H10-02; both parents are self-seedlings selections from 'Noblessa';

Asexual propagation: Cuttings, about 10 to 14 days to initiate roots; time to finish as from a 25 mm plug to a 3.8 liter container about 2 months;

Plant habit: Rounded, herbaceous perennial mound with thirty stems and compound branching beginning at base; up to 102.0 cm wide and 54.0 cm tall; average about 90.0 cm across and about 52.0 cm tall;

Stems: Cylindrical to slightly angular; upright with compound branching at every node; to 52.0 cm long and 7.0 mm diameter at base;

Internodes: About 17 nodes per stem before flowers; average about 19.0 mm apart; node color same as surround stem;

Stem color: Nearest RHS 146A;

Leaves: Alternate; linear; glabrous; acute apex; base attenuate; sessile; margin serrate; lustrous adaxial, matte abaxial; up to 5.8 cm long and 7.0 mm wide with teeth about 1.0 mm apart and 0.5 mm long;

Leaf color: Young expanding leaves adaxial nearest RHS 146B and abaxial between RHS 146B and RHS 146C; mature leaves adaxial nearest RHS 139A, abaxial nearest RHS 137B;

Veins: Pinnate; only abaxial midrib obvious; secondary adaxial and abaxial indistinct;

Adaxial midrib color: Nearest RHS 152A, distally becoming nearest RHS NN137A;

Abaxial midrib color: Nearest RHS 146D toward base, distally becoming nearest RHS NN137A;

Inflorescence: Radiate; capitate; composite consisting of ray florets; on terminal branches; about 16.0 mm diameter, about 12.0 mm tall from lower involucral bracts to top of disk florets; attitude upright to outwardly; disk about 7.0 mm across;

Inflorescence fragrance: Not detected;

Phyllaries: About 20 in two to three rows; lanceolate to deltoid; acute apex; truncate base; ciliolate margin; adaxial and abaxial glabrous; to about 4.5 mm long and 2.5 mm wide at base; inner or upper set tight against ray petals, usually eight in number, about 4.0 mm long and about 1.5 mm wide, deltoid to ovate; acute apex and truncate base, Phyllary color: Adaxial and abaxial center nearest RHS 137A, margins translucent to nearest RHS 155B;

Flowering period: Beginning mid-June in Michigan and continuing for about 7 weeks; producing up to about 200 inflorescences per stem and 1000 flowers per plant at one time;

Flower longevity: 6 to 8 days;

Flower buds: With ray florets still erect 15.0 mm wide and 8.0 mm tall, 6.0 mm across capitulum;

Flower bud color: Center ray florets while still upright nearest RHS 8C, perimeter florets nearest RHS 155D; phyllaries nearest RHS 137A;

Peduncle: Cylindrical; glaucous, thin, wiry, upright attitude, strong; about 1.5 mm wide at base and between 1.2 cm and 4.1 cm long;

Peduncle color: Nearest RHS NN137A;

Ray florets: Ligulate; imperfect; staminate; average about 110 per inflorescence;

Ray floret ligule: Oblong elongate; apex tri-lobed, lobe apices rounded; margin entire; base claw, narrowly cuneate to attenuate; opening flat to angled 90° between claw and blade; parallel veined; glabrous adaxial and adaxial; lobes about 0.3 mm long and 1.0 mm wide, blade about 5.5 mm long and about 4.0 mm wide; basal claw about 3.0 mm long and about 0.7 mm diameter;

Ray floret ligule color: Adaxial and abaxial distally nearest RHS NN155; adaxial and abaxial base nearest RHS 147D;

*Gynoecium*.—Single; about 3.5 mm long.

*Style*.—Cylindrical; about 2.0 mm long and less than 0.2 mm diameter; color nearest RHS 155D.

*Stigma*.—Bifid; about 1.0 mm long and 0.2 mm diameter; curled around 180 degrees in distal 1.0 mm; color nearest RHS 155D.

*Ovary*.—Inferior; globose; about 1.0 mm long and 1.0 mm across; color between RHS 155B and RHS 155A.

Disk florets: Rare; average less than 2 per capitulum; consisting of tepals, staminal tube and pistil; size about 6.0 mm long by 1.0 mm wide at apex;

Staminal tube: Consisting of five fused tepals;

Tepals: About 2.0 mm long; acute apices; fused into tube in basal 1.0 mm; color abaxial and adaxial nearest RHS 157D;

Androecium: Rare;

*Filament*.—(When present) cylindrical; about 0.5 mm long and less than 0.2 mm diameter; color nearest RHS 11D.

*Anther*.—(When present) connate; basifixed; longitudinal; about 1.0 mm long and 0.5 mm across; color nearest RHS 14B.

*Pollen*.—(When present) color nearest RHS 14B.

*Ray floret ligule color*.—Adaxial and abaxial distally nearest RHS NN155; adaxial and abaxial base nearest RHS 147D.

Seed: Not observed;

*Achillea* 'Peter Cottontail' is tolerant of winter temperatures as low as −35° C. and summer temperatures as high as 40° C. Once established it is also tolerant of dry summer conditions but does best with ample moisture and good drainage. It is not known to be tolerant of diseases and pest that are common to other Yarrow cultivars.

I claim:

1. The new and distinct cultivar of Yarrow plant named *Achillea* 'Peter Cottontail' as herein described and illustrated.

* * * * *